(12) United States Patent
Watanabe

(10) Patent No.: US 12,714,612 B2
(45) Date of Patent: Aug. 25, 2026

(54) DIAPER FOR PETS

(71) Applicant: Kocho Co., Ltd., Shizuoka (JP)

(72) Inventor: Kunihiko Watanabe, Shizuoka (JP)

(73) Assignee: KOCHO CO., LTD., Shizuoka (JP)

( * ) Notice: Subject to any disclaimer, the term of this patent is extended or adjusted under 35 U.S.C. 154(b) by 12 days.

(21) Appl. No.: 17/992,088

(22) Filed: Nov. 22, 2022

(65) Prior Publication Data

US 2023/0310226 A1 Oct. 5, 2023

(30) Foreign Application Priority Data

Mar. 31, 2022 (JP) ................................ 2022-059584

(51) Int. Cl.

| | |
|---|---|
| ***A61F 13/49*** | (2006.01) |
| ***A01K 23/00*** | (2006.01) |
| ***A61F 13/494*** | (2006.01) |
| ***A61F 13/56*** | (2006.01) |

(52) U.S. Cl.

CPC ........ *A61F 13/49007* (2013.01); *A01K 23/00* (2013.01); *A61F 13/49473* (2013.01); *A61F 13/5638* (2013.01); *A61F 2013/49053* (2013.01)

(58) Field of Classification Search

CPC ........... A01K 23/00; A61F 2013/49069; A61F 2013/15186

USPC ........................................................ 119/869

See application file for complete search history.

(56) References Cited

U.S. PATENT DOCUMENTS

| | | | | |
|---|---|---|---|---|
| 10,010,055 | B2 * | 7/2018 | Komatsubara | A01K 23/00 |
| 2006/0217678 | A1 | 9/2006 | Ikegami et al. | |
| 2010/0249740 | A1 * | 9/2010 | Miyamoto | D04H 1/559 428/166 |
| 2011/0209675 | A1 * | 9/2011 | Esperon | A61D 9/00 119/868 |

(Continued)

FOREIGN PATENT DOCUMENTS

| | | |
|---|---|---|
| CN | 103002845 A | 3/2013 |
| CN | 103458677 A | 12/2013 |

(Continued)

OTHER PUBLICATIONS

Office Action issued Jun. 6, 2023 in CN Application No. 202211489414.6.

(Continued)

*Primary Examiner* — Joshua D Huson
*Assistant Examiner* — Brook Victoria Schmid
(74) *Attorney, Agent, or Firm* — Panitch Schwarze Belisario & Nadel LLP

(57) ABSTRACT

Provided is a diaper for pets including: a main body used by being wrapped around a body of a pet with an inner surface kept in contact with the body of the pet; an absorbent material provided between a first end portion and a second end portion provided at ends of the main body in a lengthwise direction and absorbing liquid thereinto; gathered portions provided in the lengthwise direction with the absorbent material in between and being stretchable in the lengthwise direction; and a joint tape attached to an outer surface on a side opposite to the inner surface at the second end portion and joined to the inner surface at the first end portion. The gathered portions are provided from a side of a first edge portion of the first end portion of the main body to positions short of a second edge portion of the second end portion.

11 Claims, 6 Drawing Sheets

(56) References Cited

U.S. PATENT DOCUMENTS

2014/0076245 A1* 3/2014 Komatsubara ......... A01K 23/00 119/869
2014/0090608 A1 4/2014 Komatsubara et al.
2014/0096725 A1 4/2014 Komatsubara et al.
2014/0109843 A1 4/2014 Komatsubara et al.
2014/0123913 A1* 5/2014 Ikegami .................. A61F 13/15 119/869
2014/0165926 A1 6/2014 Marks
2016/0022506 A1 1/2016 Umebayashi
2017/0000078 A1 1/2017 Bin
2018/0325082 A1 11/2018 Komatsubara
2020/0368079 A1 11/2020 Komatsubara

FOREIGN PATENT DOCUMENTS

CN 103476248 A 12/2013
CN 111955376 A 11/2020
EP 2721924 A1 4/2014
GB 2559705 A * 8/2018 ............ A61F 13/511
JP 2003239166 A 8/2003
JP 2004001373 A 1/2004
JP 2006271212 A 10/2006
JP 2012-205576 A 10/2012
JP 2012-205577 A 10/2012
JP 2013031379 A 2/2013
JP 2014515256 A 6/2014
JP 5969175 B2 8/2016
JP 3206299 U 9/2016
WO WO-2014091849 A1 * 6/2014 ............. A01K 23/00
WO 2017/077661 A1 5/2017
WO WO-2019131067 A1 * 7/2019 ............. A01K 23/00

OTHER PUBLICATIONS

Office Action issued Nov. 25, 2025 in JP Application No. 2022113947.

* cited by examiner 1
3
5
5a
5b
7
7a
8
8a
13
13a
13b
14
14a
14b
15
17
20
L1
W1

8a
8
15
17
3
5
L1
1
7
7a
W1

DIAPER FOR PETS

CROSS-REFERENCE TO RELATED APPLICATIONS

This application claims foreign priority benefits under U.S.C. § 119 to Japanese Patent Application No. 2022-059584 filed on Mar. 31, 2022, the contents of which is hereby incorporated by reference in its entirety.

TECHNICAL FIELD

The present invention relates to a diaper for pets.

BACKGROUND ART

Diapers for pets are used for discarding excrement of pets such as dogs and cats. When pets are raised indoors, it is desirable that the diapers for pets have excellent deodorizing power and antibacterial properties and be able to be discarded through incineration and flushing into toilet bowls or the like.

According to PTL 1, non-stretching portions are provided on both sides of a diaper for pets in a lengthwise direction, so that a center part of the diaper for pets can naturally become a recessed portion when the diaper for pets is attached.

CITATION LIST

Patent Literature

PTL 1

The Publication of Japanese Patent No. 5969175

SUMMARY OF INVENTION

Technical Problem

A problem with the case of providing non-stretching portions on both sides of a diaper for pets in the lengthwise direction as in PTL 1 is that the shape cannot be maintained due to lack of rigidity of the non-stretching portions and thus it is difficult to fold end portions in the lengthwise direction when the end portions are to be folded inward at the time of attachment or disposal.

An object of the present invention, which has bee made in view of such circumstances, is to provide a diaper for pets that is easy to use at the time of attachment and disposal.

Solution to Problem

In order to solve the above problem, the diaper for pet according to the present invention adopts the following means.

A diaper for pets according to an aspect of the present invention includes: a main body that is used by being wrapped around a body of a pet with an inner surface kept in contact with the body of the pet; an absorbent material that is provided between a first end portion and a second end portion provided respectively on one end and another end of the main body in a lengthwise direction and absorbs liquid entering inside from a side of the inner surface; stretching portions that are provided in the lengthwise direction with the absorbent material in between and are stretchable in the lengthwise direction; and a joint tape that is attached to an outer surface on a side opposite to the inner surface at the second end portion and is joined to the inner surface at the first end portion, the stretching portions being provided from a side of a first edge portion of the first end portion of the main body to positions short of a second edge portion of the second end portion.

The diaper for pets is attached by being wrapped around the body of the pet and fixing the first end portion and the second end portion using the joint tape. After utilization, it is possible to obtain a disposal shape by detaching the diaper for pets from the body of the pet and folding the diaper for pets with the first end portion and the second end portion fixed using the joint tape again. At this time, the joint tape provided on the outer side of the second end portion is used to be joined to the inner surface at the first end portion.

Since the stretching portions that are stretchable in the lengthwise direction of the main body of the diaper for pets are provided up to the side of the first edge portion of the first end portion of the main body, the first end portion of the diaper for pets is easily curled with the inner surface located inside. On the other hand, the stretching portions terminate at positions short of the second edge portion of the second end portion and are not provided up to the second edge portion. Thus, the second end portion is not easily curled on the side of the inner surface like the first end portion. Therefore, it is possible to curb curling of the shape of the joint tape provided on the outer surface at the second end portion due to the stretching portions.

Rigidity is applied to the second end portion by attaching the joint tape to the outer surface at the second end portion to increase the thickness. Also, it is possible to further apply rigidity when a joint tape that is harder than the main body is used. In this manner, a bending tendency is easily applied such that the bent shape of the second end portion can be maintained when the second end portion with the joint tape attached thereto is bent. Therefore, it is possible to maintain the bent shape with the rigidity of the joint tape when the second portion is bent inward first at the time of attachment or disposal, and operability at the time of utilization is improved. Then, the inner surface at the first end portion is joined in an overlapping manner from the outer side of the second portion. At this time, the first end portion is easily curled on the side of the inner surface due to the stretching portions provided up to the side of the first edge portion and is thus easily folded, and operability is thus further improved.

Since it is possible to accommodate the joint tape provided on the outer surface at the second end portion in a manner in which the joint tape is covered with the first end portion, the joint tape does not appear in the outer appearance at the time of attachment and disposal, which leads to a good looking.

In the diaper for pets according to an aspect of the present invention, the absorbent material and the joint tape form an overlapping portion in the lengthwise direction in a plan view.

A region with rigidity is continuously formed in the lengthwise direction from the absorbent material to the joint tape by providing the overlapping portion where the absorbent material overlaps the joint tape. Since the region with rigidity at the second end portion can be continuously provided without any interruption in the lengthwise direction, rigidity of the second portion is secured, and operability is further improved.

The diaper for pets according to an aspect of the present invention further includes: flap portions that include fixed end portions fixed to the main body on outer sides of the absorbent material in a width direction and free end portions provided on sides closer to the absorbent material than the fixed end portions, the flap portions being provided in the lengthwise direction, the stretching portions being provided at the free end portions of the flap portions.

The flap portions provided in the lengthwise direction are provided, which include the fixed end portions fixed to the main body on the outer sides of the absorbent material in the width direction and the free end portions provided on the sides closer to the absorbent material than the fixed end portions. It is thus possible to surround the outer sides of the absorbent material in the width direction with the flap portions and to prevent liquid flowing into the absorbent material from leaking to the outside.

Since the stretching portions are provided at the free end portions of the flap portions, the shape of wrapping the absorbent material with the flap portions is realized, and it is possible to more reliably prevent liquid flowing into the absorbent material from leaking.

In the diaper for pets according to an aspect of the present invention, the stretching portions are provided one by one on both sides of the main body in the width direction.

It is possible to minimize the number of stretching portions by providing the stretching portions one by one on both sides of the main body. Since extra stretching portions are not provided, it is possible to simplify a manufacturing process and to realize simple design.

In the diaper for pets according to an aspect of the present invention, a plurality of projecting shapes are formed on a side of the inner surface of the absorbent material.

It is possible to hold back liquid flowing into the absorbent material with the projecting shapes by forming the plurality of projecting shapes on the side of the inner surface of the absorbent material. It is thus possible to prevent the liquid from leaking as much as possible. The projecting shapes are preferably formed with planar projecting surfaces in a repeated manner at equal intervals in the lengthwise direction and a widthwise direction that is orthogonal to the lengthwise direction. More preferably, the projecting shapes are formed at equal intervals in the lengthwise direction, are provided in a plurality of arrays in the widthwise direction, and are arranged in a zigzag shape in which each array is offset such that the projecting shapes are always present in the widthwise direction. The plurality of projecting shapes can be formed by embossing, for example.

In the diaper for pets according to an aspect of the present invention, the joint tape is a hook-and-loop fastener that is joined to a non-woven fabric, and the inner surface at the first end portion to which the joint tape is joined is a non-woven fabric.

The hook-and-loop fastener that is joined to the non-woven fabric is used as the joint tape. Thus, there is no need to separately provide a hook-and-loop fastener that is joined to the hook-and-loop fastener at the first end portion by using the non-woven fabric for the inner surface at the first end portion. In particular, when the non-woven fabric is used for the inner surface of the main body of the diaper for pets, it is possible to reduce the number of members and to achieve cost reduction.

Advantageous Effects of Invention

It is possible to realize easy utilization at the time of attachment and disposal by providing the stretching portions up to the first edge portion while not providing the stretching portions up to the second edge portion and by attaching the joint tape to the second end portion to secure rigidity.

DESCRIPTION OF EMBODIMENTS

Hereinafter, an embodiment of a diaper for pets according to the present invention will be described with reference to the drawings.

Figure 1:
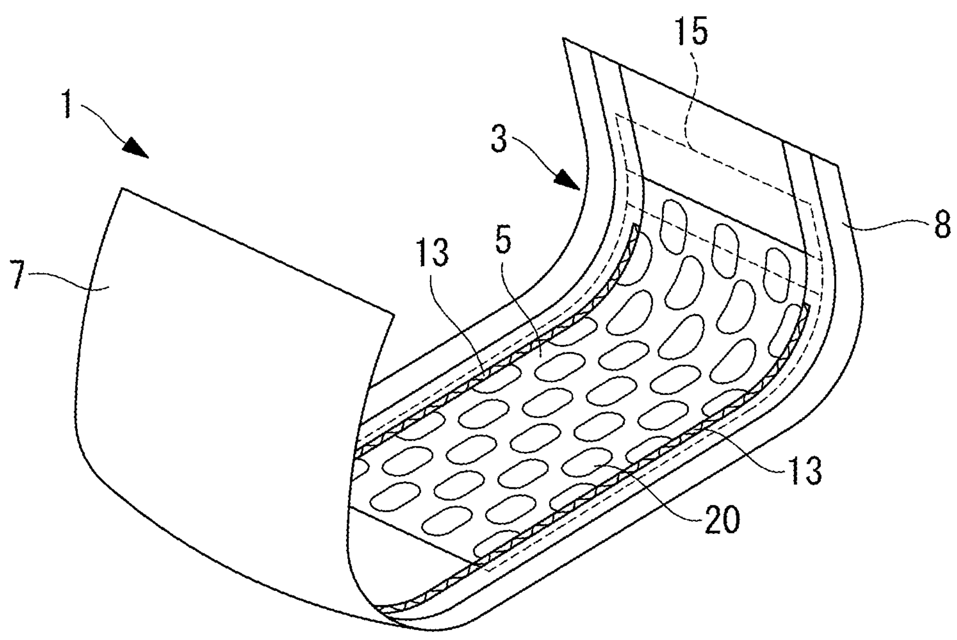
FIG. 1 is a perspective view illustrating a diaper for pets according to an embodiment of the present invention.

FIG. 1 illustrates a diaper for pets 1. The diaper for pets 1 includes a sheet-shaped main body 3 having a rectangular outer shape when the sheet-shaped main body 3 is spread in a planar shape. The main body 3 has an oblong shape in which the dimension thereof in a lengthwise direction L1 is larger than the dimension thereof in a width direction W1. An absorbent material (absorber) 5 is provided at the center of the main body 3. The absorbent material 5 has a function of absorbing and retaining liquid such as excrement of a pet and includes, for example, a water absorbent polymer.

Figure 2:
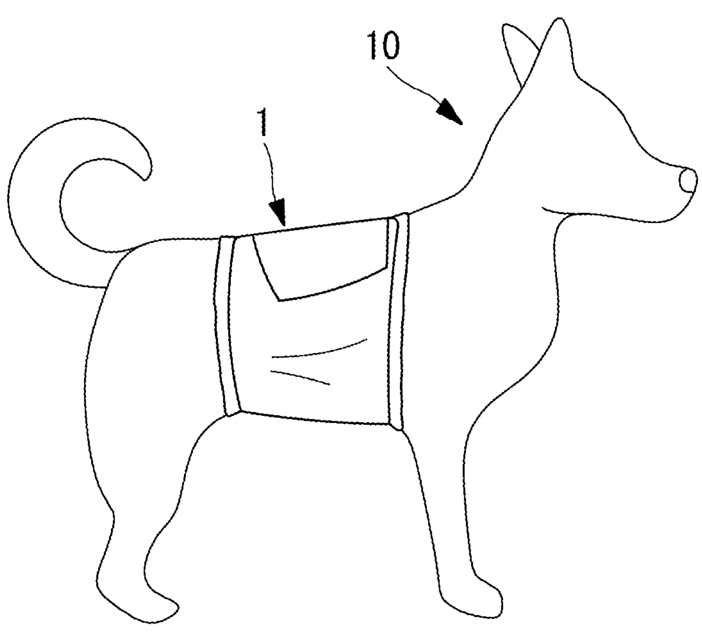
FIG. 2 is a perspective view illustrating a state in which the diaper for pets in FIG. 1 is attached to a dog.

As illustrated in FIG. 2, the diaper for pets 1 is attached to a dog (pet) by being wrapped around a body of the pet 10 with the front surface side of the absorbent material 5 facing the body of the dog 10. In other words, the diaper for pets 1 is in the form of a so-called belly band.

Figure 3:
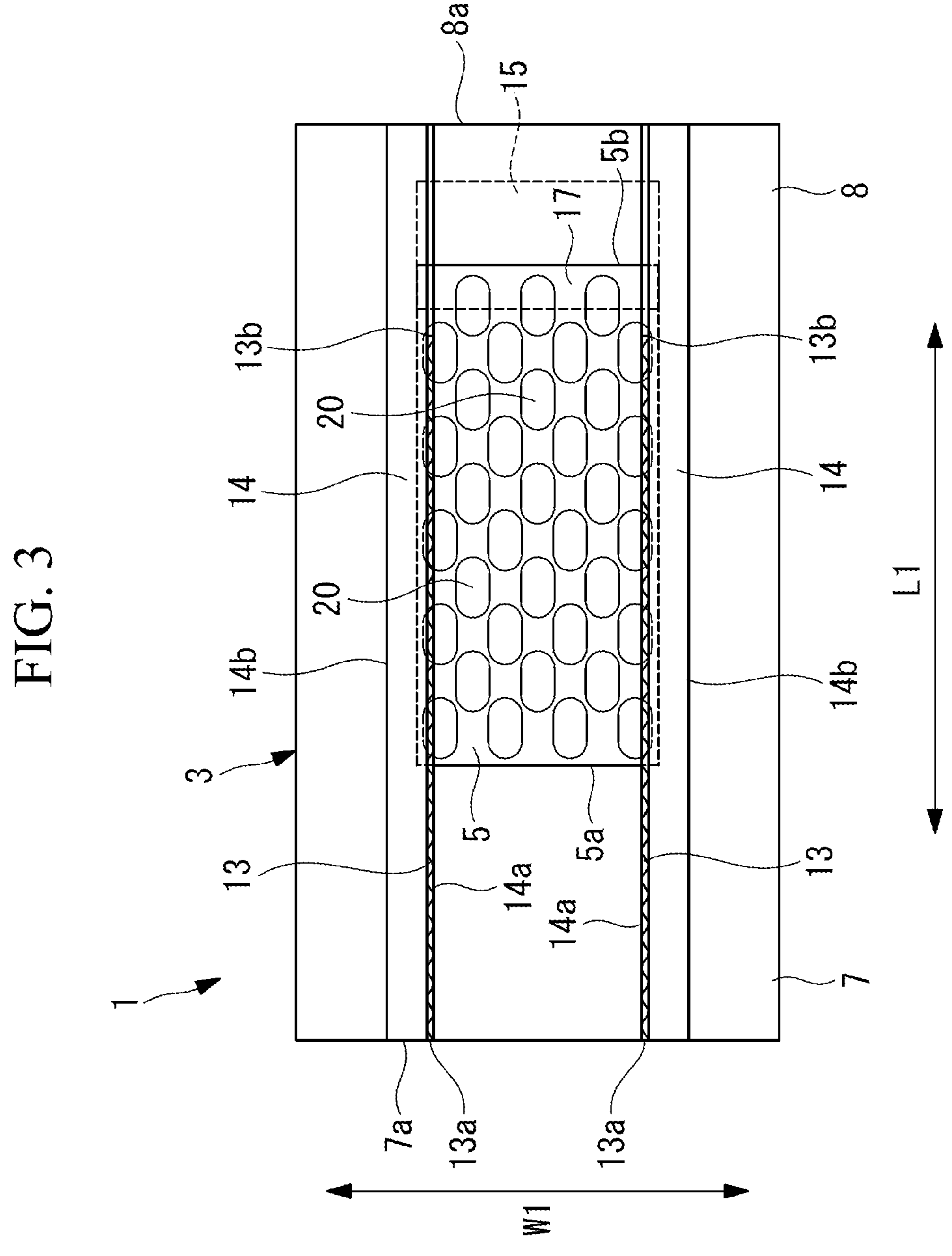
FIG. 3 is a plan view when an inner surface of the diaper for pets in FIG. 1 is seen.
Figure 4:
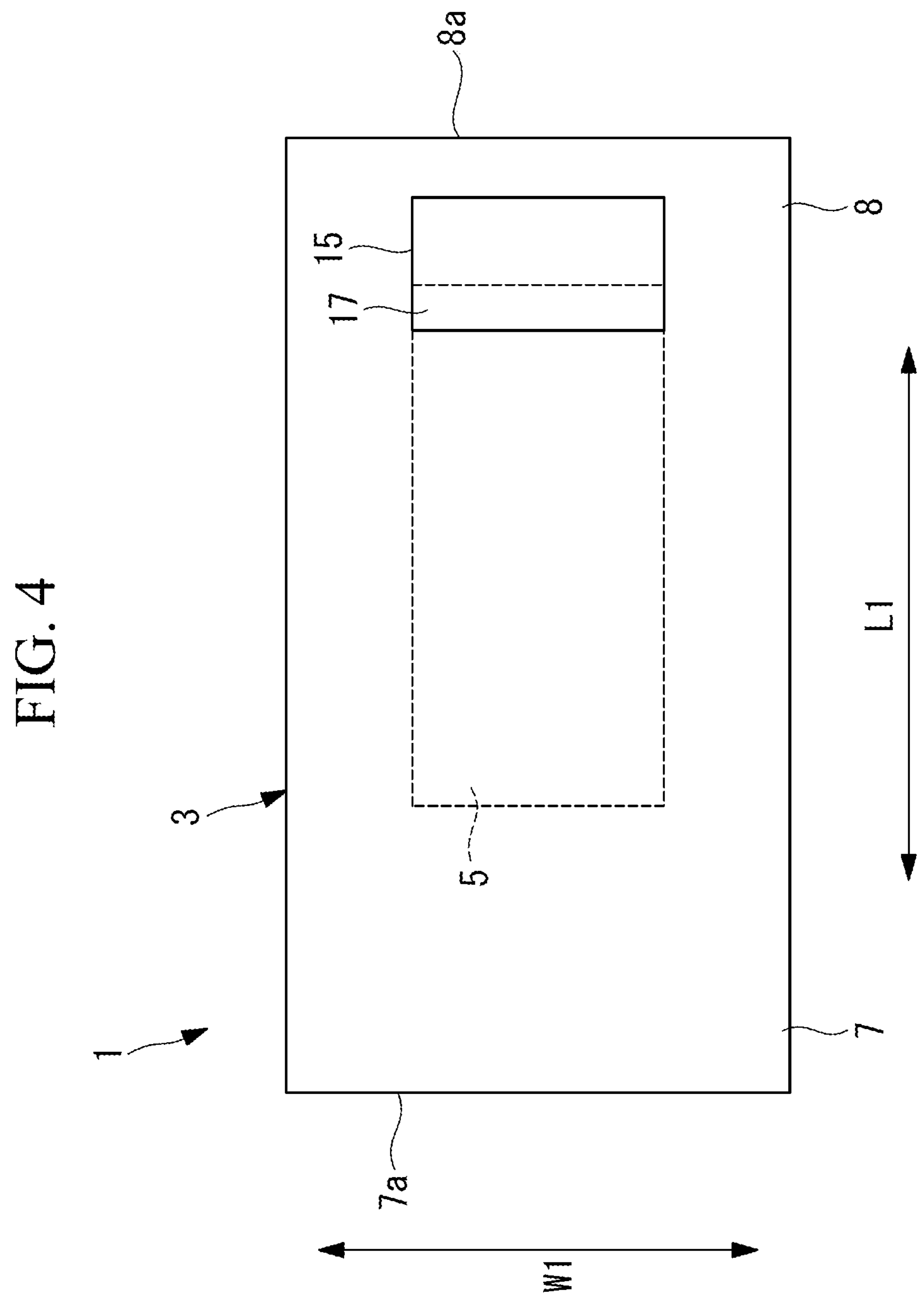
FIG. 4 is a back surface view when an outer surface of the diaper for pets in FIG. 1 is seen.

FIG. 3 illustrates a planar view of a state where the diaper for pets 1 is opened. The drawing illustrates a state in which the diaper for pets 1 is seen from the side of the inner surface.

The main body 3 is made of a non-woven fabric, and surface treatment for liquid impermeability and the like are performed on the side of the outer surface (the rear side in FIG. 3).

The absorbent material 5 provided at the center of the main body 3 has a rectangular sheet shape in a plan view. The width dimension of the absorbent material 5 in the width direction W1 of the main body 3 is smaller than the width dimension of the main body 3.

A first end portion 7 and a second end portion 8 are provided respectively on one side and the other side of the absorbent material 5, that is, at one end portion and the other end portion of the main body 3 in the lengthwise direction L1.

Gathered portions (stretching portions) 13 are provided one by one at both side portions of the absorbent material 5 in the width direction W1. In other words, further stretching portions that are stretchable in the lengthwise direction L1 are not provided on the outer sides beyond the gathered portions 13 in the width direction W1. Therefore, the stretching portions are not provided at both edge portions of the main body 3 in the width direction W1.

Figure 5:
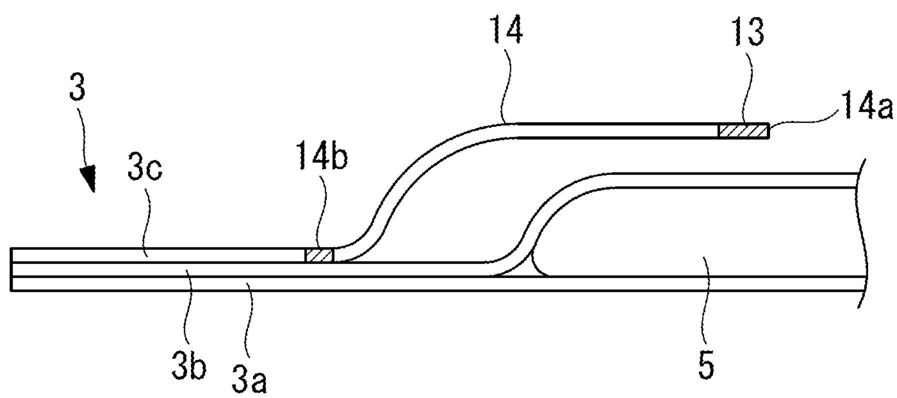
FIG. 5 is a partial cross-sectional view illustrating a periphery of one of flap portions.

The gathered portions 13 are stretchable in the lengthwise direction L1. The gathered portions 13 are three-dimensionally provided to cover the side portions of the absorbent material 5 in the width direction W1 from the upper side. Specifically, the gathered portions 13 are provided at free end portions 14*a* of flap portions 14 as illustrated in FIG. 5. The flap portions 14 include the fixed end portions 14*b* fixed to the main body 3 and the free end portions 14*a* located on the sides closer to the absorbent material 5 than the fixed end portions 14*b*. The free end portions 14*a* are not fixed to the main body 3 and the absorbent material 5 at the center portion in the lengthwise direction L1, and the flap portions 14 on the sides of the free end portions 14*a* thereby stand up from the fixed end portions 14*b* as start points. Note that both end sides of the free end portions 14*a* in the lengthwise direction are fixed to the absorbent material 5 or the main body 3 as will be described later.

The flap portions 14 are formed using a third layer 3*c* in the main body 3 which is composed of a first layer 3*a*, a second layer 3*b*, and the third layer 3*c* as illustrated in FIG. 5. The absorbent material 5 is disposed in a sandwiched manner between the first layer 3*a* and the second layer 3*b*.

Note that the present invention is not limited to the main body 3 composed of the three layers 3*a*, 3*b*, and 3*c*. Therefore, it is enough for the flap portions 14 to have the fixed end portions 14*b* fixed to the main body, and the flap portions 14 may not be formed as parts of the main body 3.

The flap portions 14 hold back the liquid guided to the side of the absorbent material 5. Also, the main body 3 is biased to be curled inward via the flap portions 14 with a stretching force of the gathered portions 13 by the gathered portions 13 being provided on the side closer to the front surface (the side closer to the inner surface) than the absorbent material 5.

As illustrated in FIG. 3, the gathered portions 13 extend in the lengthwise direction L1 from first termination portions 13*a* on the side of the first end portion 7 to second termination portions 13*b* on the side of the second end portion 8. The first termination portions 13*a* of the gathered portions 13 reaches the side of a first edge portion 7*a* that is an edge portion of the main body 3 on the side of the first end portion 7.

Note that it is not necessary for the first termination portions 13*a* to be located at the same positions as that of the first edge portion 7*a* in a strict sense, and deviation is allowed to some extent. That is, it is enough for the first termination portions 13*a* to be provided to such an extent that stretching deformation caused by the gathered portions 13 reaches the first edge portion 7*a*. In other words, it is only necessary for the first termination portions 13*a* to be provided within a range of equal to or less than 20 mm (preferably, equal to or less than 15 mm, or more preferably, equal to or less than 10 mm) from the first edge portion 7*a*.

The second termination portions 13*b* of the gathered portions 13 are provided at positions short of a second edge portion 8*a* that is an edge portion of the second end portion 8 of the main body 3. The second termination portions 13*b* are located at positions before reaching a second edge portion 5*b* of the absorbent material 5 on the side of the second end portion 8. Moreover, the second termination portions 13*b* are located before the joint tape 15 (on the side of the first end portion 7) such that the second termination portions 13*b* do not overlap the range where the joint tape 15 is attached.

Note that the second termination portions 13*b* may be provided up to positions exceeding the absorbent material 5 on the side of the second edge portion 8*a* or positions at which the second termination portions 13*b* overlap the joint tape 15. However, the second termination portions 13*b* are not provided to extend up to positions exceeding the joint tape 15 on the side of the second edge portion 8*a*. In other words, the gathered portions 13 are not provided beyond the joint tape 15 on the side of the second edge portion 8*a*.

The free end portions 14*a* of the flap portions 14 are fixed to the absorbent material 5 or the main body 3 from the side of the absorbent material 5 in the vicinity of the first edge portion 5*a* of the absorbent material 5 to the first end portion 7 of the main body 3 and from the side of the absorbent material 5 in the vicinity of the second edge portion 5*b* of the absorbent material 5 to the second end portion 8 of the main body 3. This prevents liquid from leaking in the lengthwise direction L1 along the flap portions 14.

The joint tape 15 is a hook-and-loop fastener that is joined to a non-woven fabric. The joint tape 15 is attached through adhesion, for example, to the outer surface (the side of the rear surface) of the main body 3. In regard to material of the joint tape 15, a resin-based material having higher rigidity than the non-woven fabric, for example, is used, and specifically, polypropylene is used.

The joint tape 15 has a rectangular shape and has a width dimension that is similar extent to that of the absorbent material 5. The joint tape 15 forms an overlapping portion 17 that overlaps a part of one end portion of the absorbent material 5 in the lengthwise direction L1 in a plan view as in FIG. 3. Only the non-woven fabric constituting the main body 3 is present beyond the joint tape 15 on the side of the second edge portion 8*a*.

The non-woven fabric is present on the inner surface at the first end portion 7 that comes into contact with the joint tape 15 at the time of joining such that the non-woven fabric can be detachably joined to the joint tape 15. Note that a tape that is suitably joined to the joint tape 15 may be provided on the inner surface of the first end portion 7.

As illustrated in FIGS. 1 and 3, a plurality of projecting portions (projecting shape) 20 with projecting shapes are formed on the side of the inner surface of the absorbent material 5.

Each projecting portion 20 has a planar upper surface and has an oval shape in a plan view. The long axis of the oval shape is directed in the lengthwise direction L1. The projecting portions 20 are repeatedly formed at equal intervals in the lengthwise direction L1 and the width direction W1. More specifically, the projecting portions 20 are formed at equal intervals in the lengthwise direction, are provided in a plurality of arrays in the width direction W1, and are arranged in a zigzag shape in which each array is offset such that the projecting portions 20 are always present in the width direction W1. Each projecting portion 20 can be formed by embossing, for example.

Note that the shape of the projecting portions 20 may be another shape instead of the oval shape.

The aforementioned diaper for pets 1 is used as follows.

As illustrated in FIG. 2, the diaper for pets 1 is put around the body of the dog 10 with the absorbent material 5 facing the body of the dog 10 when the diaper for pets 1 is attached to the dog 10. Then, the first end portion 7 and the second end portion 8 are joined to each other by laying the first end portion 7 over the second end portion 8 with the first end portion 7 located outside the second end portion 8 and with the non-woven fabric on the inner surface at the first end portion 7 coming into contact with the joint tape 15.

At the time of disposal after utilization, the joint tape 15 is peeled off from the non-woven fabric on the inner surface at the first end portion 7, and the diaper for pets 1 is removed from the dog 10. Then, the diaper for pets 1 is folded such that the second end portion 8 covers the absorbent material 5 and is then folded such that the inner side at the first end portion 7 overlaps the joint tape 15 at the second end portion 8. In this manner, a disposal shape in which the absorbent material 5 of the diaper for pets 1 is covered with the second end portion 8 and the first end portion 7 is achieved, and the diaper for pets 1 is discarded into a trash can or the like.

The diaper for pets 1 according to the present embodiment has the following working effects.

Since the gathered portions 13 that are stretchable in the lengthwise direction L1 of the main body 3 of the diaper for pets 1 are provided up to the side of the first edge portion 7*a* of the first end portion 7 of the main body 3, the first end portion 7 of the diaper for pets 1 is easily curled with the inner surface located inside. On the other hand, the gathered portions 13 are terminated at positions short of the second edge portion 8*a* of the second end portion 8, are not provided up to the second edge portion 8*a*. Thus, the second end portion 8 is not easily curled on the side of the inner surface like the first end portion 7. Therefore, it is possible to curb curling of the shape of the joint tape 15 provided on the outer surface at the second end portion 8 due to the gathered portions 13.

Rigidity is applied to the second end portion 8 by attaching the joint tape 15 to the outer surface at the second end portion 8 to increase the thickness. Also, it is possible to further apply rigidity since the joint tape 15 that is harder than the main body 3 is used. In this manner, a bending tendency is easily applied such that the bent shape of the second end portion 8 can be maintained when the second end portion 8 with the joint tape 15 attached thereto is bent. Therefore, it is possible to maintain the bent shape with the rigidity of the joint tape 15 when the second end portion 8 is bent inward first at the time of attachment or disposal, and operability at the time of utilization is improved. Then, the inner surface at the first end portion 7 is joined in an overlapping manner from the outer side of the second portion 8. At this time, the first end portion 7 is easily curled on the side of the inner surface due to the gathered portions 13 provided up to the side of the first edge portion 7*a* and is thus easily folded, and operability is thus further improved.

Since it is possible to accommodate the joint tape 15 provided on the outer surface at the second end portion 8 in a manner in which the joint tape 15 is covered with the first end portion 7, the joint tape 15 does not appear in the outer appearance at the time of attachment and disposal, which leads to a good looking.

A region with rigidity is continuously formed in the lengthwise direction L1 from the absorbent material 5 to the joint tape 15 by providing the overlapping portion 17 where the absorbent material 5 overlaps the joint tape 15. Since the region with rigidity at the second end portion 8 can be continuously provided without any interruption in the lengthwise direction L1, rigidity of the second portion 8 is secured, and operability is further improved.

The flap portions 14 provided in the lengthwise direction L1 are provided, which include the fixed end portions 14*b* fixed to the main body 3 on the outer sides of the absorbent material 5 in the width direction W1 and the free end portions 14*a* provided on the sides closer to the absorbent material 5 than the fixed end portions 14*b*. It is thus possible to surround the outer sides of the absorbent material 5 in the width direction W1 with the flap portions 14 and to prevent liquid flowing into the absorbent material 5 from leaking to the outside.

Since the gathered portions 13 are provided at the free end portions 14*a* of the flap portions 14, the shape of wrapping the absorbent material 5 with the flap portions 14 is realized, and it is possible to more reliably prevent liquid flowing into the absorbent material 5 from leaking.

It is possible to minimize the number of gathered portions 13 by providing the gathered portions 13 one by one on both sides of the main body 3. Since extra gathered portions 13 are not provided, it is possible to simplify a manufacturing process and to realize simple design.

It is possible to hold back liquid flowing into the absorbent material 5 with the projecting portions 20 by forming the plurality of projecting portions 20 on the side of the inner surface of the absorbent material 5. It is thus possible to prevent the liquid from leaking as much as possible.

The hook-and-loop fastener that is joined to the non-woven fabric is used as the joint tape 15. Thus, there is no need to separately provide a hook-and-loop fastener that is joined to the hook-and-loop fastener at the first end portion 7 by using the non-woven fabric as a material for the inner surface 7 at the first end portion 7. In particular, since the inner surface of the main body 3 of the diaper for pets 1 is made of the non-woven fabric, it is possible to reduce the number of members and to achieve cost reduction.

Note that although the aforementioned embodiment has been described on the assumption that the diaper for pets 1 is applied to a dog, the present invention is not limited thereto and may be applied to other pets such as a cat.

Figure 6:
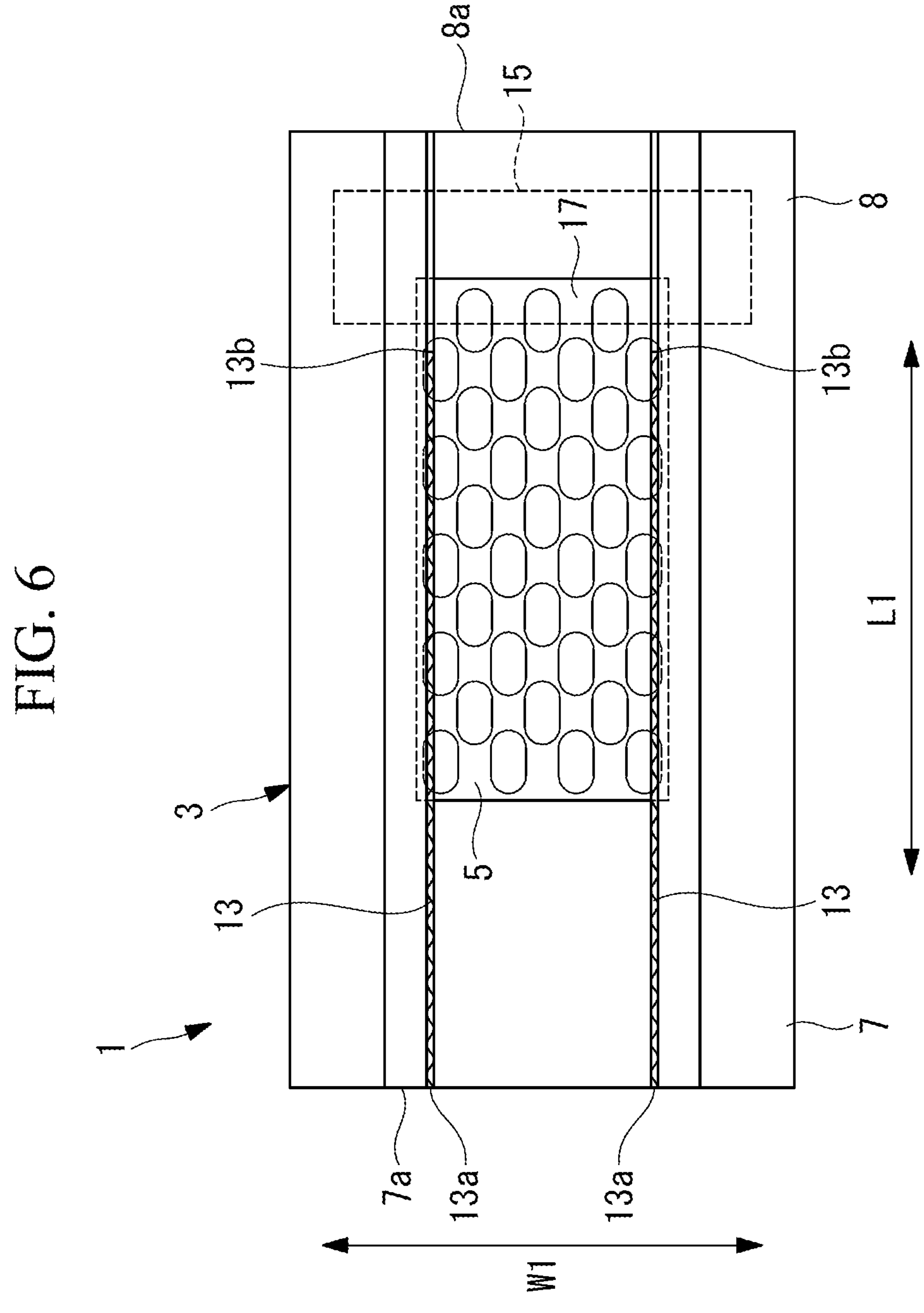
FIG. 6 is a plan view of a diaper for pets illustrating a modification of a width dimension of a joint tape.

Although the aforementioned joint tape 15 has a width dimension that is similar extent to the width of the absorbent material 5, the joint tape 15 may be provided substantially over the entire main body 3 in the width direction W1 as illustrated in FIG. 6.

REFERENCE SIGNS LIST

1 Diaper for pets
3 Main body
5 Absorbent material (absorber)
5*a* First edge portion
5*b* Second edge portion
7 First end portion
7*a* First edge portion
8 Second end portion
8*a* Second edge portion
10 Dog (pet)
13 Gathered portion (stretching portion)
13*a* First termination portion
13*b* Second termination portion
14 Flap portion
14*a* Free end portion
14*b* Fixed end portion
15 Joint tape
17 Overlapping portion
20 Projecting portion (projecting shape)

The invention claimed is:

1. A diaper for pets comprising:

a main body configured to be wrapped around a body of a pet with an inner surface kept in contact with the body of the pet and that has a rectangular outer shape, wherein the main body has a first end portion provided at one end in a lengthwise direction of the rectangular outer shape and a second end portion provided at another end in the lengthwise direction of the rectangular outer shape;

a rectangularly shaped absorbent material that is positioned between the first end portion of the main body and the second end portion of the main body, the absorbent material being configured to absorb liquid entering inside from a side of the inner surface;

stretching portions that are provided in the lengthwise direction with the absorbent material in between and are stretchable in the lengthwise direction; and flap portions that include fixed end portions fixed to the main body on outer sides of the absorbent material in a width direction of the main body and free end portions provided on sides closer to the absorbent material than the fixed end portions, the flap portions being provided in the lengthwise direction, wherein:

the main body has an outer, liquid impermeable sheet and an inner sheet made of a non-woven fabric, the absorbent material is disposed in a sandwiched manner between the outer sheet and the inner sheet, a rectangularly shaped joint tape is attached to the outer sheet at the second end portion of the main body, the joint tape being configured to join to the inner sheet at the first end portion of the main body, the stretching portions consisting of gathered portions provided at the free end portions of the flap portions, the stretching portions are not provided on outer sides of the gathered portions in the width direction such that the stretching portions are not provided at both edge portions of the main body in the width direction, the main body has a first edge defined by an outer periphery of the first end portion and a second edge defined by an outer periphery of the second end portion, the absorbent material has a first edge located on a side closer to the first end portion of the main body and a second edge located on a side closer to the second end portion of the main body, the main body has a first side and a second side, each of the first side and the second side extending along the lengthwise direction of the main body on each side of the width direction of the main body, the gathered portions comprise a first stretching portion and a second stretching portion, and the first stretching portion is provided on the first side of the main body and the second stretching portion is provided on the second side of the main body, each of the first stretching portion and the second stretching portion has a first termination portion located on a side closer to the first edge of the main body and a second termination portion located on a side closer to the second edge of the main body, the first termination portions of the first stretching portion and the second stretching portion are each positioned within 20 mm or less from the first edge of the main body, and the second termination portions of the first stretching portion and the second stretching portion are each positioned short of the second edge of the absorbent material on a side of the second edge of the main body.

2. The diaper for pets according to claim 1, wherein:

the joint tape is a hook-and-loop fastener that is configured to join to a non-woven fabric, the diaper has an overlapping portion in which a part of an end portion of the absorbent material on a side of the second edge of the absorbent material in a direction along the lengthwise direction of the main body and the joint tape overlap in a thickness direction via the outer sheet, in an open configuration of the diaper viewed from a side of the inner surface;

in the lengthwise direction of the joint tape, the joint tape consists of a portion forming the overlapping portion and a non-overlapping portion that does not overlap with the absorbent material; and the second termination portions of the first stretching portion and the second stretching portion are each located in a position short of the second edge of the absorbent material and short of the joint tape in the lengthwise direction of the main body so as to be out of a range of the overlapping portion.

3. The diaper for pets according to claim 1, wherein the gathered portions comprise only the first and second stretching portions.

4. The diaper for pets according to claim 1, wherein a plurality of projecting shapes are formed on the inner sheet above the absorbent material.

5. The diaper for pets according to claim 1, wherein the inner surface at the first end portion to which the joint tape is configured to join is a non-woven fabric.

6. The diaper for pets according to claim 1, wherein a width dimension of the joint tape is substantially equal to a width of the absorbent material or has a length extending over substantially the entire main body in the width direction.

7. A diaper for pets comprising:

a main body configured to be wrapped around a body of a pet with an inner surface kept in contact with the body of the pet and that has a rectangular outer shape, wherein the main body has a first end portion provided at one end in a lengthwise direction of the rectangular outer shape and a second end portion provided at another end in the lengthwise direction of the rectangular outer shape;

a rectangularly shaped absorbent material that is positioned between the first end portion of the main body and the second end portion of the main body, the absorbent material being configured to absorb liquid entering inside from a side of the inner surface;

stretching portions that are provided in the lengthwise direction with the absorbent material in between and are stretchable in the lengthwise direction; and flap portions that include fixed end portions fixed to the main body on outer sides of the absorbent material in a width direction and free end portions provided on sides closer to the absorbent material than the fixed end portions, the flap portions being provided in the lengthwise direction, wherein:

the main body has an outer, liquid impermeable sheet and an inner sheet made of a non-woven fabric, the absorbent material is disposed in a sandwiched manner between the outer sheet and the inner sheet, a rectangularly shaped joint tape is attached to the outer sheet at the second end portion of the main body, the joint tape being configured to join to the inner sheet at the first end portion of the main body, the joint tape being a hook-and-loop fastener that is configured to join to a non-woven fabric, the stretching portions consist of gathered portions provided at the free end portions of the flap portions, the main body has a first edge at an end of the first end portion and a second edge at an end of the second end portion, the absorbent material has a first edge located on a side closer to the first end portion of the main body and a second edge located on a side closer to the second end portion of the main body, the main body has a first side and a second side, each of the first side and the second side extending along the lengthwise direction of the main body on each side of a width direction of the main body, the gathered portions comprise a first stretching portion and a second stretching portion, and the first stretching portion is provided on the first side of the main body and the second stretching portion is provided on the second side of the main body, each of the first stretching portion and the second stretching portion has a first termination portion located on a side closer to the first edge of the main body and a second termination portion located on a side closer to the second edge of the main body, an overlapping portion is defined by an entire area where the absorbent material and the joint tape overlap in an open configuration of the diaper, in the lengthwise direction of the joint tape, the joint tape consists of a portion forming the overlapping portion and a portion forming a non-overlapping portion that does not overlap with the absorbent material, wherein the non-overlapping portion extends from the second edge of the absorbent material toward the second edge of the main body in the lengthwise direction, and the second termination portions of the first stretching portion and the second stretching portion each end in the lengthwise direction short of the overlapping portion.

8. The diaper for pets according to claim 7, wherein the gathered portions comprise only the first and second stretching portions.

9. The diaper for pets according to claim 7, wherein a plurality of projecting shapes is formed on the inner sheet above the absorbent material.

10. The diaper for pets according to claim 7, wherein the inner surface at the first end portion to which the joint tape is configured to join is a non-woven fabric.

11. The diaper for pets according to claim 7, wherein a width dimension of the joint tape is substantially equal to a width of the absorbent material or has a length extending over substantially the entire main body in the width direction.

* * * * *